United States Patent
Wiesner et al.

(10) Patent No.: US 9,052,270 B2
(45) Date of Patent: Jun. 9, 2015

(54) HEATABLE GAS SENSOR AND METHOD FOR THE PRODUCTION THEREOF

(76) Inventors: Manfred Wiesner, Bendorf (DE); Andreas Kechter, Lahnstein (DE)

(*) Notice: Subject to any disclaimer, the term of this patent is extended or adjusted under 35 U.S.C. 154(b) by 467 days.

(21) Appl. No.: 13/512,189

(22) PCT Filed: Nov. 23, 2010

(86) PCT No.: PCT/EP2010/007077
§ 371 (c)(1),
(2), (4) Date: Jul. 18, 2012

(87) PCT Pub. No.: WO2011/063925
PCT Pub. Date: Jun. 3, 2011

(65) Prior Publication Data
US 2012/0272720 A1    Nov. 1, 2012

(30) Foreign Application Priority Data
Nov. 25, 2009 (DE) .......................... 10 2009 054 435

(51) Int. Cl.
*G01N 27/12* (2006.01)
*G01N 33/00* (2006.01)

(52) U.S. Cl.
CPC .......... *G01N 27/12* (2013.01); *Y10T 29/49117* (2015.01); *G01N 33/004* (2013.01); *G01N 33/005* (2013.01)

(58) Field of Classification Search
CPC . G01N 27/12; G01N 27/4047; G01N 27/125; G01N 33/005; G01N 33/0037; G01N 33/004; G01N 33/0054; G01N 27/4073
See application file for complete search history.

(56) References Cited

U.S. PATENT DOCUMENTS

| | | | | |
|---|---|---|---|---|
| 3,092,799 A * | 6/1963 | Baker | | 338/34 |
| 3,676,820 A * | 7/1972 | Taguchi | | 338/34 |
| 3,865,550 A * | 2/1975 | Bott et al. | | 436/151 |
| 4,347,732 A * | 9/1982 | Leary | | 73/31.05 |
| 4,541,988 A * | 9/1985 | Tozier et al. | | 422/94 |
| 4,596,975 A | 6/1986 | Reddy et al. | | |
| 4,601,914 A * | 7/1986 | Barnes et al. | | 438/49 |
| 4,723,439 A | 2/1988 | Asakura et al. | | |
| 4,731,226 A | 3/1988 | Takahata et al. | | |
| 4,755,473 A | 7/1988 | Nishino et al. | | |
| 4,849,180 A * | 7/1989 | Fukui | | 422/98 |
| 4,896,143 A * | 1/1990 | Dolnick et al. | | 340/634 |
| 5,439,581 A * | 8/1995 | Schmah | | 204/427 |
| 5,448,905 A * | 9/1995 | Stetter et al. | | 73/31.05 |
| 5,767,388 A * | 6/1998 | Fleischer et al. | | 73/31.06 |
| 6,012,327 A * | 1/2000 | Seth et al. | | 73/31.06 |
| 6,319,473 B1 | 11/2001 | Ozaki et al. | | |
| 6,499,335 B2 * | 12/2002 | Nomura et al. | | 73/31.06 |
| 7,180,076 B2 * | 2/2007 | Haverstick et al. | | 250/382 |
| 2010/0045610 A1 * | 2/2010 | Hong et al. | | 345/173 |

FOREIGN PATENT DOCUMENTS

DE    20 05 497 A1    11/1970
DE    4139721 C1 *    6/1993 ............ G01N 27/14
(Continued)

*Primary Examiner* — David A Rogers
(74) *Attorney, Agent, or Firm* — Fay Sharpe LLP (57) ABSTRACT

The invention relates to a heatable gas sensor for gases containing reducing substances, comprising a gas-sensitive porous metal oxide and electrical elements spaced apart from one another both for heating the metal oxide and for measuring a conductivity of the metal oxide, wherein each electrical element is spatially embedded in the metal oxide. The invention further relates to a method for producing the gas sensor.

12 Claims, 6 Drawing Sheets

(56) References Cited

FOREIGN PATENT DOCUMENTS

| | | | |
|---|---|---|---|
| DE | 199 24 611 A1 | 12/2000 | |
| DE | 19924083 A1 * | 12/2000 | ........... G01N 27/407 |
| EP | 0464243 A1 * | 1/1992 | |
| EP | 0527259 A1 * | 2/1993 | |

* cited by examiner

HEATABLE GAS SENSOR AND METHOD FOR THE PRODUCTION THEREOF

FIELD OF THE INVENTION

The invention relates to a heatable gas sensor and a method for producing the same.

TECHNICAL BACKGROUND

For detection and optional determination of the concentration of substances such as methane, ethane, propane, carbon monoxide, hydrogen, etc. in gas mixtures, heating gases, exhaust gases and/or the like, gas sensors based on inorganic metal oxide semiconductors (MOX) are known from the state of the art. When such gas sensors, which are designed as a porous solid, come in contact with the aforementioned substances or other reducing substances, the conductivity of the metal oxide changes at least at its surface. The change in conductivity of the metal oxide can be detected and analyzed by means of an electronic unit to detect reducing substances and optionally determine their concentration.

Such a gas sensor is known from DE 44 28 155 C2. The gas sensor comprises a substrate on which an interdigital electrode structure is created in the form of two comb-like intermeshing electrical elements that are spaced a distance apart from one another. A layer of gas-sensitive metal oxide, gallium oxide here, is applied to the interdigital electrode structure and is in contact with the same. On coming in contact with a flammable gas, the conductivity of the metal oxide changes and the gas concentration can be determined accordingly by measuring the electrical resistance between the two electrical elements of the interdigital comb-like intermeshing electrode structure spaced a distance apart from one another.

However, the changing conductivity of the gas-sensitive metal oxide is a function of temperature. Therefore in DE 44 28 155 C2 a temperature sensor is provided as a separate element on the substrate in proximity to the interdigital electrode structure. The actual temperature of the gas sensor must thus be ascertained and taken into account in analyzing the measured resistance values.

If the temperature is too low, the gas sensor known from DE 44 28 155 C2 cannot be used because an electron transition of the adsorbed molecules of the reducing substances, causing a change in conductivity, takes place in a quantity that can be analyzed reasonably only at temperatures above 450° C. in the case of gallium oxide. Gallium oxide is thus an n-type conductor at temperatures above approximately 450° C. In the range between approximately 450° C. and 700° C., gallium oxide has a strong sensitivity to reducing substances, such as methane, ethane, propane, carbon monoxide, hydrogen and the like which is a result of surface interactions. Therefore the entire gas sensor is limited to use purposes in which the gas to be monitored has a sufficiently high temperature. This is the case with exhaust gases of combustion processes, for example.

To be able to use a gas sensor based on metal oxide even at lower ambient temperatures, EP 0 464 244 B1 describes also providing an electrical element for heating on a substrate which has comb-like intermeshing electrical elements that are spaced a distance apart from one another for measuring the conductivity of the metal oxide. The electrical element for heating is embodied in the form of a meandering printed conductor, which may carry a heating current and is situated on the surface of the substrate opposite the electrical elements for measuring the conductivity of the metal oxide. It is thus possible to heat the metal oxide, which is again embodied as gallium oxide, to a temperature above 450° C.

Due to the design of the electrical elements for heating the metal oxide on one side of a substrate and for measuring a conductivity of the metal oxide on the opposite side of the substrate, this yields disadvantages with the gas sensor known from EP 0 464 244 B1. Thus, on the one hand, production is complex and expensive but on the other hand, the heating energy does not act directly on the metal oxide surrounding the electrical elements for measuring the metal oxide but instead acts through the substrate. Finally, the sensitivity of the sensor is not optimal because there is only a limited amount of metal oxide between the electrical measurements for measuring the metal oxide and the sensor is gas-sensitive on only one side.

Under typical use conditions, the sensors are exposed to high temperatures up to 1200° C., mechanical stresses in the form of vibrations and thermal stresses due to extreme temperature changes and must also be able to withstand chemical influences due to reducing and corrosive gas components over long periods of time without undergoing any significant aging, so there are weaknesses in principle with the known substrate-based sensors, which must be compensated by increased technical complexity. With the gas sensor known from EP 0 464 244 B1, passivation by means of silicic acid is necessary to prevent catalytic reactions on the open surfaces of the heating arrangement. In vaporization of the passivation layer due to the aforementioned adverse operating conditions, there are negative effects on the sensitivity of the gas sensor. Furthermore, the substrate may be excited to vibrations, and thermal stresses may lead to damage to the electrical elements on the substrate.

Finally, production of a substrate-based gas sensor such as that known from the DE 44 28 155 C2 or EP 0 464 144 B1 is technically complex and expensive because special equipment is required to form small structures on a substrate.

Although U.S. Pat. No. 3,835,529 describes a substrate-free gas sensor based on an inorganic metal oxide semiconductor, no heating element is provided in the substrate-free embodiment to heat the metal oxide. When a heating element is present, it is applied to a backing, which is a substrate that must also be heated. This leads to the disadvantages mentioned above. Furthermore, a cylindrical, gas-impermeable metal housing is obligatory with the gas sensor known from U.S. Pat. No. 3,835,529 because the metal oxide is present in a loose powder form. The gas-impermeable housing reduces the sensitivity of the sensor because gas cannot reach the sensor on all sides and instead the gas must flow through end caps to the sensor. Furthermore, heating of the gas sensor results in unfavorable inherent thermal conditions. Finally, the loose packing of the metal oxide has a negative effect on the signal stability because mechanical stresses such as vibrations interfere with the contact structure.

With the gas sensor known from DE 10 2008 055 568 A1 the electrical elements for heating are designed separately from the electrical elements for performing measurements. No electrical elements are provided here to be used jointly for heating and measuring and none are embedded spatially in metal oxide. Instead DE 10 2008 055 568 A1 discloses a classical layer structure.

With the gas sensor known from DE 198 59 998 A1 the measurement elements are arranged on a substrate. This is fundamentally problematical because there may be faulty flows. The substrate is recessed between measurement elements, and the metal oxide layer applied over the measurement elements extends into the recess. A heater designed separately from the measurement elements is uncoupled from the sensitive layer.

The gas sensor of DE 44 01 570 A1 does not have a heating element, is not sensitive on all sides and requires a third electrode which is insulated from a semiconductor layer.

Finally DE 690 18 742 T2 discloses a thermistor and a gas sensor with this thermistor wherein the heater is designed separately from the thermistor. Furthermore, the thermistor does not have porous material and the gas sensor is not sensitive on all sides.

Against this background, the object of the invention is to create a heatable gas sensor and a method for producing same according to the preamble of claim 1 and/or 6 which will permit a longer use time even under adverse use conditions while achieving an increased sensitivity and simplifying the design in a manner that also lowers manufacturing costs.

DESCRIPTION OF THE INVENTION

This object is achieved by a heatable gas sensor and a method of manufacturing same.

Accordingly, a heatable gas sensor for gases which contain reducing substances such as methane, ethane, propane, carbon monoxide, hydrogen and/or the like, with a gas-sensitive porous metal oxide and electrical elements spaced a distance apart from one another, is created for heating the metal oxide and for measuring the conductivity of the metal oxide, in which the elements are each embedded in sintered metal oxide.

The gas sensor according to the invention is thus free of a substrate, and the sintered metal oxide surrounds the electrical elements on all sides.

Therefore, this first yields an increased sensitivity because the conductivity is measured in a three-dimensional spatial area along and between the electrical elements, such that this area offers a much larger internal surface of the porous metal oxide, in comparison with the known two-dimensional layer structure, on which reactions with the reducing substances can take place.

Furthermore, there is no longer any directional dependence. The gas sensor according to the invention is instead sensitive to gas on all sides and need not be aligned directionally.

Furthermore, thermal stresses due to changing temperatures are largely prevented because only the electrical elements and the metal oxide are provided but there is no substrate or heating core nor are there any other layers and elements such as a housing, each having different thermal expansion coefficients.

Production of such a sensor is also simpler and less expensive because no processing of the substrate is necessary nor is a housing necessary.

The combined use of the electrical elements for heating and for measurement yields a heating effect directly at the measurement site and simplifies the design and production because a separate heating need not be provided. Thus an embedded element may be used for heating, and another element which is also embedded may be used for measuring the current or voltage in the meantime.

Finally, sintering the metal oxide increases both the mechanical stability and the signal stability of the gas sensor. The sensor signal also remains stable over a long term regardless of the mechanical influences acting from the outside.

The gas-sensitive metal oxide preferably comprises gallium oxide, aluminum oxide or a mixture of gallium oxide and aluminum oxide, but other metal oxides may also be used.

An adequate porosity, so that a measurable surface interaction may take place between the reducing substance and the metal oxide, is important. The measure of porosity, which depends on the thickness of the metal oxide and in particular depends on the distance between the electrical elements for measuring the conductivity, can be determined in the usual manner as a function of thickness. The open porosity is preferably 10% to 75% and in particular between 30% and 50% and preferably approximately 50%. The determination of the open porosity of sintered samples is performed using the water penetration method according to DIN EN 623, Part 2. The principle is based on the fact that a porous body undergoes an increase in mass when its externally accessible pores are filled with fluid. The open porosity is dimensionless and therefore can be given in percentage. An open porosity of 50%, for example, means that 50% of the body is filled with open pores. With a theoretical density of $2.7 \text{ g/cm}^3$ and an open porosity of 50%, this would yield a gross density of $1.35 \text{ g/cm}^3$ in simplified terms.

Expediently at least one of the elements for heating the metal oxide can carry electricity. The element can therefore carry a heating current which results in heating due to the resistance of the electrical element. This heating occurs directly in the area of the metal oxide which is located next to the element. In this way the spatial area of the porous metal oxide in which the change in conductivity is measured can be heated directly. No foreign bodies such as substrates or heating element carriers are present and therefore need not be heated and they also do not limit the spatial measurement area. The result is a good thermal stability. Since the measurement result depends to a great extent on the temperature of the metal oxide, this also results in an improvement in the stability of the measurement.

Another electrical element which is arranged at a distance from the element that can carry an electrical current for heating the metal oxide may be used in a preferred embodiment to measure the conductivity of the metal oxide between the two elements. To this end the resistance between the at least one element that can carry an electrical current to heat the metal oxide and the additional element may be measured. The element carrying the current thus serves to heat the metal oxide and to measure the conductivity.

The additional one of the elements may also carry an electrical current for heating the metal oxide.

The electrical elements may thus be used for both heating and measuring. For example, two electrical elements may be provided with a distance between them, each element having two electrical terminals leading to the outside. In this case both electrical elements may carry electrical current for heating the metal oxide and it is possible to measure the conductivity of the metal oxide between the two elements. It also possible to provide one of the elements with two electrical terminals leading to the outside, while another has only one terminal. It is also possible to provide more than two elements.

Preferably at least two elements extend with a distance between them so that they are parallel, meandering, spiral-shaped and/or in the form of a double helix in at least some sections. The spatial area of the metal oxide between the elements, which is used to measure the conductivity, can be enlarged by using such structures.

Furthermore, the present invention also creates a method for producing a heatable gas sensor, in particular according to any one of the preceding embodiments, wherein at least two electrical elements are arranged at a distance from one another so that they are embedded spatially with a distance apart from one another in the gas-sensitive porous metal oxide.

This simplifies the production process in comparison with a substrate-based gas sensor with which electrical structures must be applied to a substrate and must be coated.

Supporting means here ensure the distance between the two electrical elements. The supporting means is a suitable aid for ensuring a three-dimensional structure of electrical elements. The supporting means may have a comb-like structure and/or may be used in the joint production of the electrical elements, e.g., in joint winding, laying, folding or forming or the like and also in separate production of the electrical elements it may also be used in joining of the same. The supporting means may be removed after the joint formation or joining even before the joint structure is embedded in metal oxide. As an alternative to this, the supporting means may be removed only after being embedded in metal oxide or during the embedding process. At any rate the supporting means ensure that a three-dimensional structure is embedded in the metal oxide. The supporting means may also be used after inserting the electrical structures into the mold and/or embedding them to establish the desired distance between them. In addition to the supporting function, it may also fulfill a calibration function.

Production may be accomplished by injection molding, press molding, casting or film casting methods. It is preferable to embed the electrical elements in metal oxide powder such that the metal oxide powder is sintered with the embedded elements following at least one fire and optionally two or more fires. The sintering is preferably performed at temperatures above 1200° C. and in particular at temperatures in a range between 1400° C. and 1600° C., where the best results can be achieved in the range from 1400° C. to 1500° C. The sintering temperature and the choice of the metal oxide powder with regard to granularity and additional properties and also the pressure for compaction exerted on the metal oxide powder before sintering are to be selected in accordance with the sintering temperature and duration so that the required open porosity is obtained, taking into account the thickness of the gas sensor.

Production is especially simple when at least the metal oxide powder is introduced into a mold and the electrical elements are placed on the layer of metal oxide powder with a distance between them. The elements may then be covered with another layer of metal oxide and sent for the sintering process.

To be able to control the distance between the elements, according to another embodiment of the invention it is possible to first introduce metal oxide powder into a mold, then apply an element, for example, in a meandering form, to the metal oxide powder, to cover the element with a layer of metal oxide powder, to apply another element, for example, also in a meandering form, and to also cover this with metal oxide powder before sintering.

The aforementioned components as well as the components that have been claimed and used as described according to the invention in the exemplary embodiments are not subject to any particular exceptional conditions in their size, shape, choice of materials and technical conception so that the selection criteria known in the field of use may be applied without restriction.

Additional details, features and properties of the subject matter of the invention are derived from the claims as well as from the following description and the figures in which exemplary embodiments are shown as examples. Individual features of the claims or of the specific embodiments may be combined with other features of other claims and other specific embodiments.

BRIEF DESCRIPTION OF THE FIGURES

FIGS. 1(a), (b) and (c) illustrate a gas sensor according to the invention in a perspective view, in a longitudinal section and in cross section.

DETAILED DESCRIPTION OF EXEMPLARY EMBODIMENTS

Figures 1A, 1B:
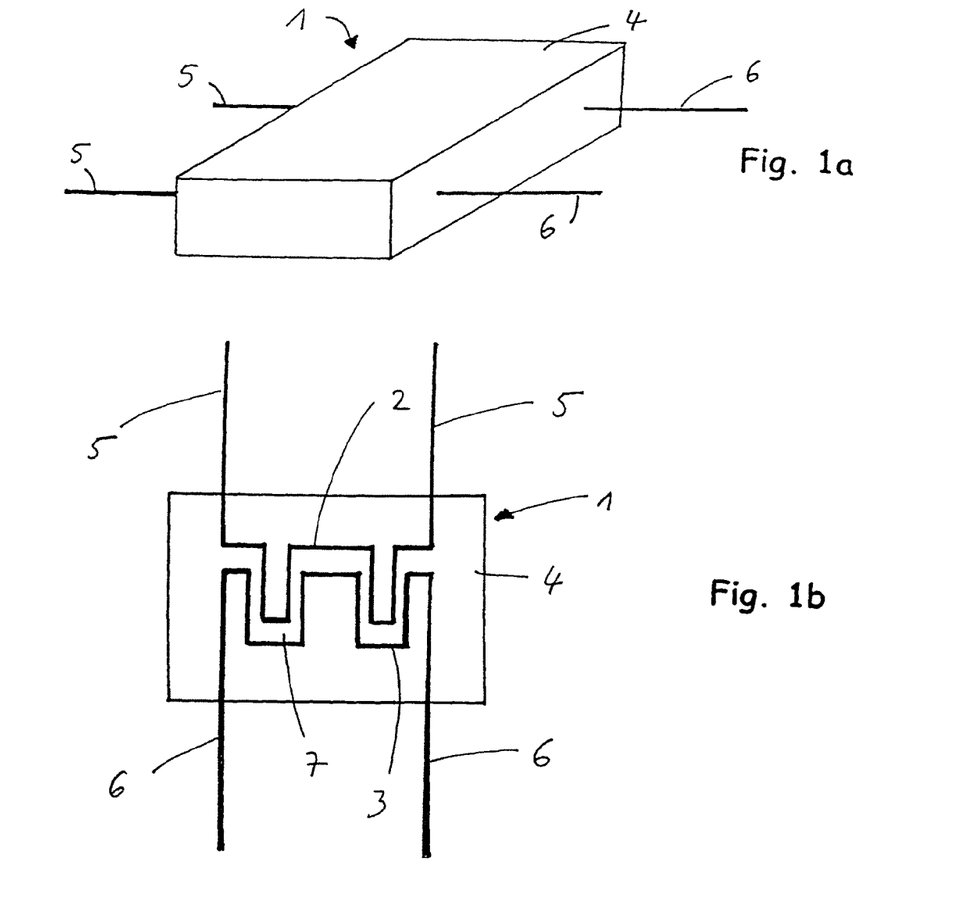
Figure 1C:
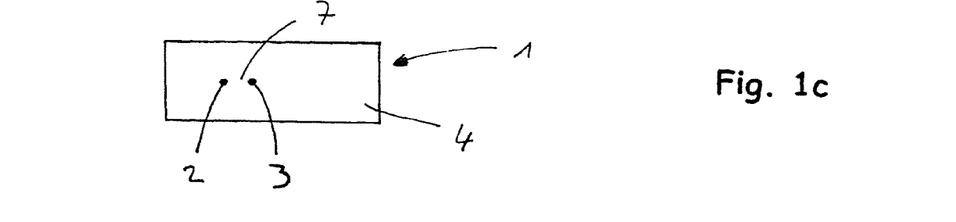

The gas sensor 1 shown in the form of a cube in FIG. 1, for example, has two electrical elements 2, 3, which are embedded in a metal oxide 4 and can be contacted here via terminals 5, 6 leading out of the sensor 1 at the sides, for example.

The metal oxide, for example, gallium oxide, aluminum oxide or a mixture thereof is preferably shaped into a shallow shape which may have the dimensions of 7 mm×2 mm×7 mm, for example, in the case of the cube-shaped design, shown as an example. In other specific embodiments, the metal oxide may be spherical, oval, coin-shaped or the like.

The electrical elements 2, 3, which are embedded in the metal oxide, i.e., surrounded by metal oxide on all sides, may be formed from thin metal wire. A suitable material for the metal wire is a simple copper alloy, but those with corrosion resistance in aggressive environments because of noble metals such as Pt, An, Rh, etc. are preferred, having a diameter of 0.01 to 1 mm, for example, preferably 0.1 to 0.3 mm. The two electrical elements 2, 3 each have a section which is shaped in a meandering form, for example, in which they run with a slight distance between them of 0.1 to 2 mm, for example, in particular 0.1 to 0.5 mm or 1 mm. Due to this distance, a three-dimensional area 7 is formed along and between the electrical elements 2, 3. The conductivity of this three-dimensional area 7 can be determined, for example, by measuring the resistance. To do so, a voltage can be applied between the terminals 5, 6 and the current flow can then be determined. The conductivity measured in this way is a measure of the concentration of reducing substances, which have been absorbed on the metal oxide.

The gas sensor 1 can be heated, for example, by sending electricity through the electrical element 2. To do so, a voltage difference may be applied between the terminals 5, leading to a current flow through the electrical element 2 from one of the terminals 5 to the other one of the terminals 5. This current flow is converted by the resistance of the electrical element 2 into heat. The resulting thermal energy heats up the metal oxide. This heating occurs directly in the three-dimensional area 7 along and between the elements 2, 3 which is used for the measurement. Heating of the gas sensor 1 may also occur due to the other electrical element 3 in addition or alternatively. In other embodiments additional electrical elements may also be provided for heating and/or measuring. The temperature regulation and stabilization of the heating may be accomplished via the change in resistance of the electrical element which forms a heating wire.

Figure 2A:
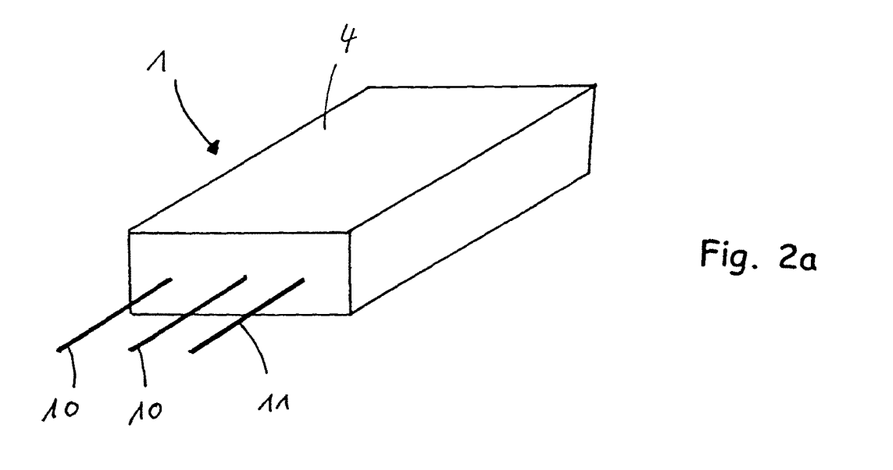
FIGS. 2(a) and (b) illustrate another embodiment of a gas sensor according to the invention in a perspective view and in a longitudinal view.
Figure 2B:
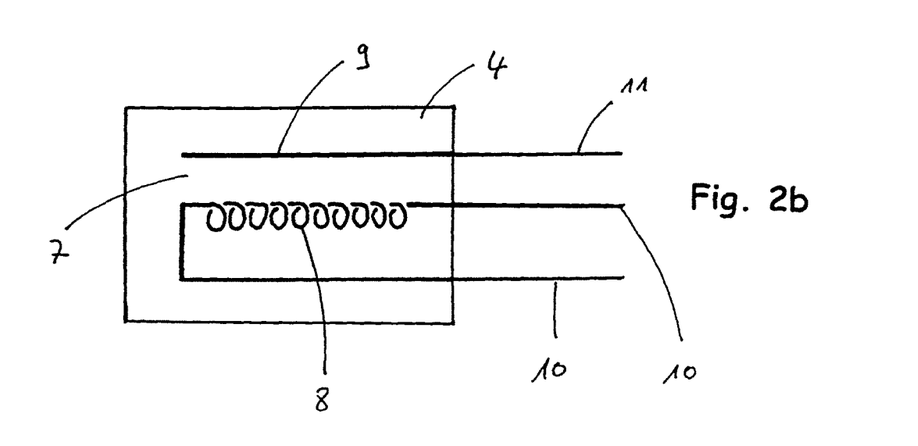

The gas sensor 1 shown in FIG. 2 has two electrical elements 8, 9 of a different design.

The electrical element 8 comprises a section the form of a spiral and two terminals 10 are led out of the gas sensor 1 at the end face where they are parallel to one another. The electrical element 8 can be used as a heating element by means of the two terminals 10 in that it receives electricity which is converted into thermal energy in the spiral section.

A section of the electrical element 9, which has only one electrical terminal 11, is adjacent to the electrical element 8. The conductivity in the area 7 between the neighboring sections of the electrical elements 8, 9 can be measured in this embodiment by, for example, the voltage between the terminals 10 on the one hand and the terminal 11 on the other hand and measuring the current flow between the terminals 10 and terminal 11.

In other embodiments, the electrical elements may have additional section designs in the neighboring sections. For example, the electrical elements may run strictly parallel to one another or may form a kind of helix structure. It is important that the distance is such that a measurement is reasonably possible at the desired operating temperatures. Examples of distances between the electrical elements vary on the order of a few tenths of millimeters up to 2 mm.

Figure 3A:
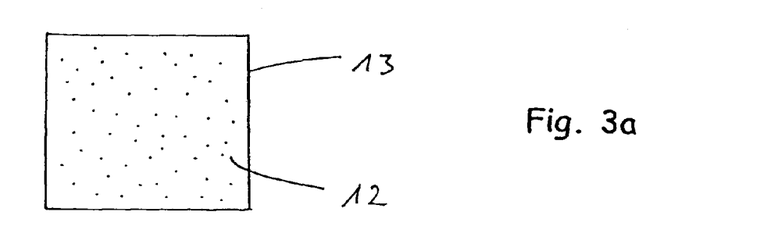
FIGS. 3(a), (b) and (c) illustrate steps of a method according to the invention for producing a gas sensor.
Figure 3B:
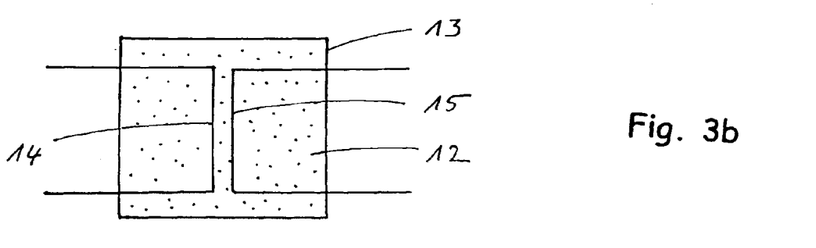
Figure 3C:
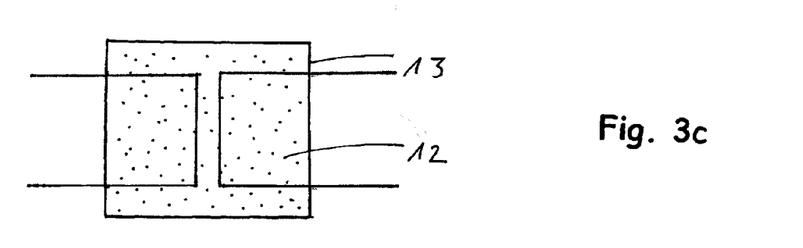

The method according to the invention for producing a gas sensor, as illustrated in FIG. 3, comprises essentially encasing metal oxide powder 12 in a mold 13, which is shown in a view from above in FIG. 3(*a*). Then electrical elements, for example, two electrical elements 14, 15 here having parallel sections running a distance apart from one another and placed flat over an area (cf. FIG. 3(*b*)) are applied to this optionally flattened layer. Finally the mold 13 containing the metal oxide powder 12 is then filled until the electrical elements 14, 15 are completely covered (cf. FIG. 3(*c*)). In conclusion, sintering may optionally be performed after compacting the metal oxide powder.

The sintering is preferably performed at temperatures above 1200° C. Preferred temperature ranges for sintering are from 1200° C. to 1600° C. in particular from 1400° C. to 1500° C. This increases the mechanical strength and resistance to temperature fluctuations as well as the corrosion resistance of the gas sensor. The result is a porous ceramic.

In the production process, it is necessary to ensure that the distance between the electrical elements remains a desired extent in at least some sections and that an adequate porosity is formed. The porosity is necessary in order that the gas to be measured and with it the reducing substances can penetrate into the sensor and can react with the surface, in particular also in the spatial area 7 along and between the electrical elements. Open porosity in the range between 10% and 75% is selected here and is preferably approximately 40% to 50%. Furthermore, the open porosity counteracts stresses in the material which occur due to thermal fluctuations.

Another production process according to the invention will now be described in greater detail with reference to FIGS. 4 and 5.

Figure 4A:
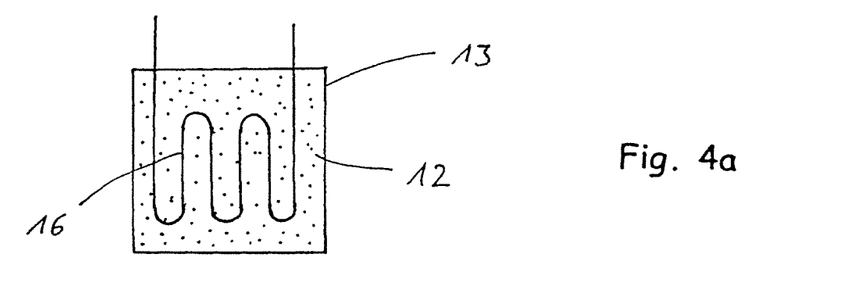
FIGS. 4(a), (b) and FIGS. 5(a), (b) illustrate steps of another method according to the invention for producing a gas sensor.
Figure 4B:
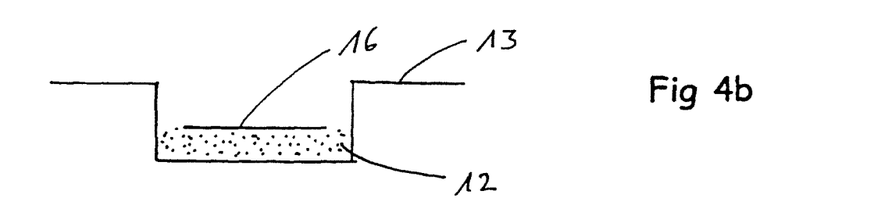
Figure 5A:
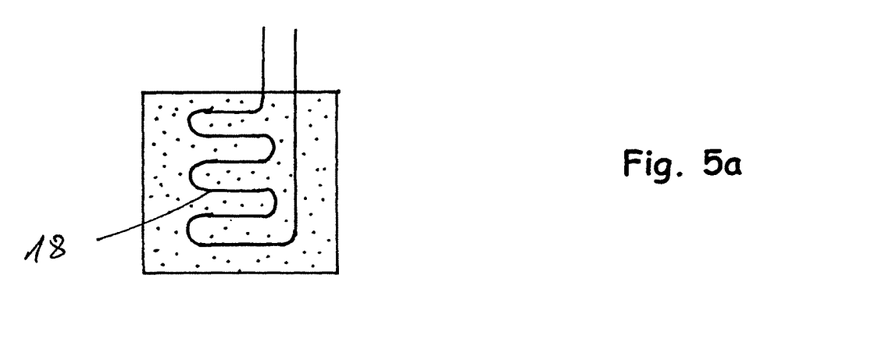

According to this metal oxide powder 12 is introduced into a mold 13 and optionally compacted there and then an electrical element 16 is applied, designed here in a meandering form, for example (cf. the view of the mold 13 from above in FIG. 4(*a*) and the cross section in FIG. 4(*b*)).

Figure 5B:
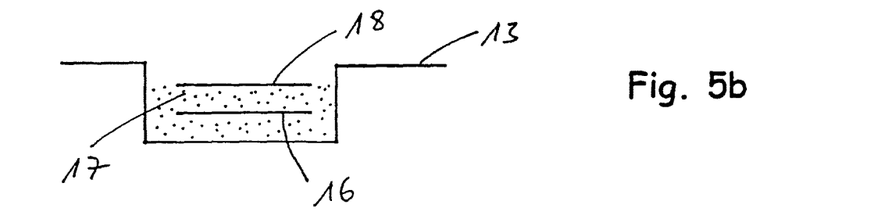

Next a layer 17 (cf. the cross section through the mold 13 in FIG. 5(*b*)) is applied and optionally compacted, so that the layer 17 ensures a distance between the electrical element 16 and another electrical element 18 which is applied to the layer 17 and is also shown here with a meandering shape as an example. Finally, the second electrical element 18 is covered with metal oxide powder and subjected to a sintering process, optionally after being compacted.

The method illustrated in FIG. 6 for producing the gas sensor uses a filling technique. First electrical elements 20 are inserted into an empty mold 13 having four contact bushings 19 on the bottom (cf. the view from above in FIG. 6(*a*)), such that the electrical elements are expediently a distance away from one another and also from the bottom 21 of the mold 13 (cf. the cross section and the view from above in FIGS. 6(*b*) and (*c*)).

Figure 6A:
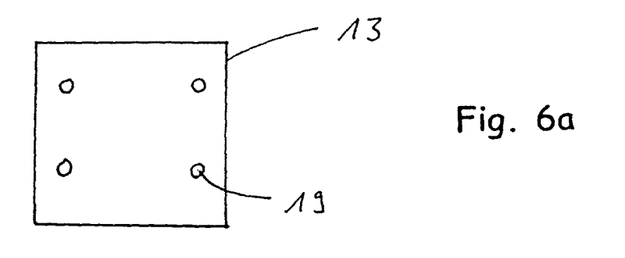
FIGS. 6(a), (b), (c) and (d) illustrate steps of another method according to the invention for producing a gas sensor in a view from above and in a section through a mold.
Figure 6B:
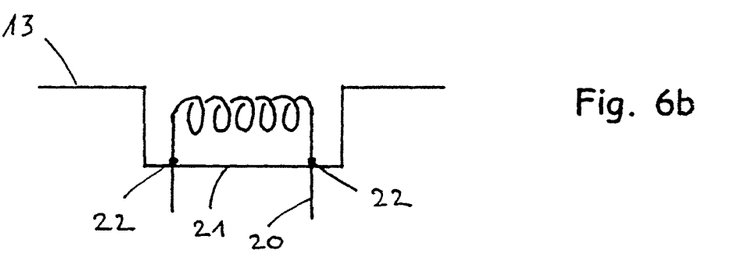
Figure 6C:
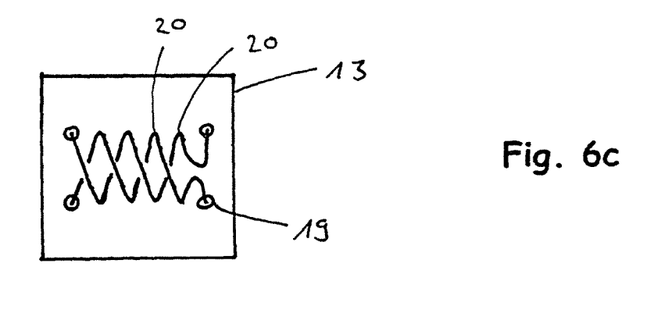
Figure 6D:
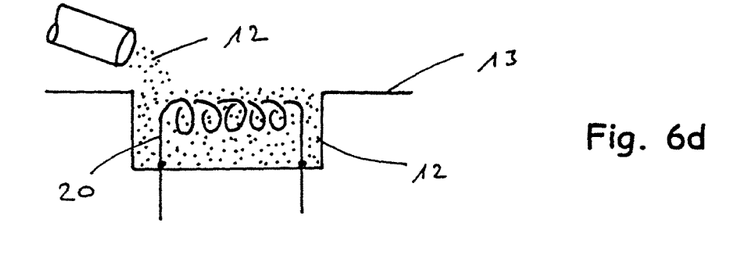

The electrical elements 20 are shown here in coil form as an example with a coil axis running parallel to the longitudinal axis of the gas sensor, which is shown here as having a cube shape, for example. The electrical elements 20 preferably at any rate extend parallel to one another in the area of the coils at the expedient distances mentioned above. The distance can be ensured by an auxiliary structure such as a comb-like intermeshing spacer element engaging in the coil windings as seen from above or by spacer pins or thickened areas or coatings on the electrical elements 20.

The distance from the bottom 21 of the mold 13 may be ensured, for example, by compressing the electrical elements 20 together in spots for the purpose of forming widened areas 22 which are broader than the diameter of the contact bushings 19.

After position the electrical elements 20 in the mold 13, the mold 13 can be filled with metal oxide in one step (cf. FIG. 6(*d*)). Then it may optionally be sintered under pressure.

The metal oxide powder, for example, gallium oxide powder, may have a grain size of approximately 10 μm.

In other embodiments the gas sensors are produced by means of casting, injection molding and film casting methods, all of which can be used with the aforementioned methods, in particular according to FIGS. 3 through 6, with the provision that the metal oxide powder (MOX) is supplied in the form of a mixture.

In one embodiment the gas sensor is produced by means of a casting method. The MOX powder mixture is processed to form a ceramic slurry by means of water, dispersant and binders in a suitable dispersing apparatus. A standard recipe for the casting slurry consists of:
100 g MOX powder mixture
20-30 g water (dispersing medium)
0.3-0.9 g diammonium citrate (dispersant)
0.01-0.03 g methyl cellulose (binder)

The slurry is cast in the mold in which the electrodes and/or electrical elements are situated. After the slurry has cured and dried, the greenware is unmolded and processed.

In another embodiment, the gas sensor is produced in an injection molding process. To do so an MOX powder mixture is processed to form granules by using binders and additives. These granules are heated to the softening point/melting point of the binders and are pressed while hot into the mold, which already contains the electrical elements (injection molding). A conventional recipe for this consists of:
100 g MOX powder mixture
20-40 g polyacrylic acid (PMMA)
5-10 g oleic acid Finally, the gas sensor can also be produced with a film casting method. To do so, the MOX powder mixture is processed to form a ceramic slurry by adding alcohol, dispersant, plasticizers and binders to a suitable dispersing apparatus. The standard recipe for the film casting slurry consists of:

100 g MOX powder mixture
40-60 g ethylene (dispersant medium)
10-14 g dimethyl phthalate (plasticizer)
10-20 g ethyl cellulose (binder)

This slurry is poured into a funnel which has a gap at the lower end that defines the height and width of the substrate. The slurry is cast through the gap onto a plastic film. The film is supported on a roller and is drawn past the gap and beneath it, forming a plastic ceramic film in which the electrical elements are embedded. After the ceramic film has dried, the shape required for the gas sensor is cut out or punched out.

Then a sintering process is performed in all the embodiments.

In the embodiments shown here the terminals 5, 6, 10, 11 are each led out of the gas sensor 1 at the side or at the bottom. In other embodiments, other contacts with the electrical elements 2, 3, 8, 9 14, 15, 16, 18 may be provided, for example, in the form of exposed contact faces.

Figure 7:
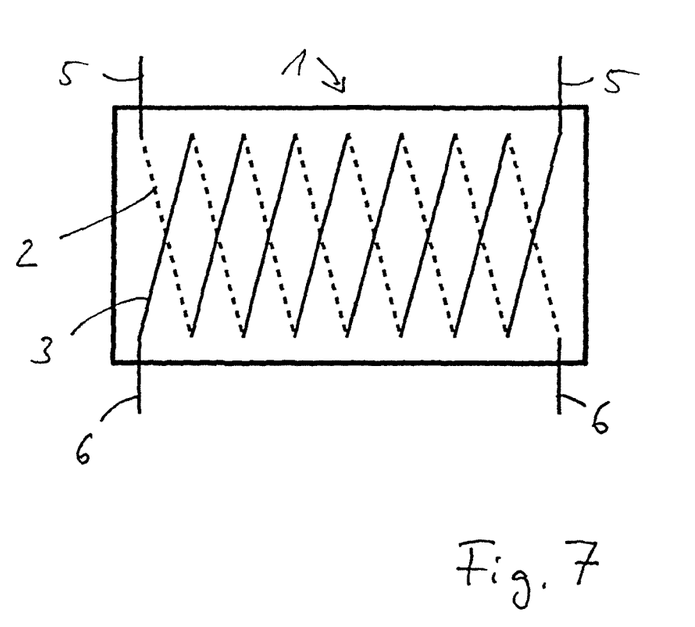
FIG. 7 illustrates another embodiment in a view from above.

FIG. 7 shows another embodiment with two electrical elements 2, 3 coiled in the form of a helix. The broken line is located at the bottom in the view from above whereas the solid line is always located at the top. The two elements 2, 3 which are coiled in the form of a spiral are ideally always spaced an equal distance apart from one another. Therefore, supporting means may be used, for example, a comb structure, or the elements 2, 3 may be embedded in wax or the like. The supporting means may be used in the combined production of the two elements 2, 3 or in joining the elements 2, 3 that have been produced separately and removed before insertion into a mold or thereafter and optionally during or after embedding in metal oxide or they may also remain there permanently.

LIST OF REFERENCE NUMERALS

1 gas sensor
2, 3, 8, 9, 14, 15, 16, 18, 20 electrical element
4 metal oxide
5, 6, 10, 11 terminal
7 area
12 metal oxide powder
13 mold
17 layer
19 contact bushings
21 bottom
22 widened areas

The invention claimed is:

1. A heatable gas sensor for gases containing reducing substances, having a gas-sensitive porous metal oxide and electrical elements which are spaced a distance apart from one another and heat the metal oxide and measure a conductivity of the metal oxide, characterized in that at least two electrical elements are each embedded in the sintered metal oxide and at least one of the electrical elements is designed for heating the metal oxide as well as for measuring the conductivity in cooperation with another electrical element, said at least two electrical elements are arranged at said distance from one another by using supporting means and are embedded in gas-sensitive porous metal oxide, and the metal oxide is sintered.

2. The gas sensor according to claim 1, characterized in that at least one of the electrical elements for heating the metal oxide can conduct electricity.

3. The gas sensor according to claim 2, characterized in that a voltage and/or a current can be measured between the at least one element which can receive electricity for heating the metal oxide and the additional electrical element for measuring the conductivity of the metal oxide between the electrical elements.

4. The gas sensor according to claim 3, characterized in that the additional one of the electrical elements can receive electricity for heating the metal oxide.

5. The gas sensor according to claim 1, characterized in that at least two electrical elements extend parallel, meandering, in a spiral and/or double helix in at least some sections in the metal oxide.

6. A method for producing a heatable gas sensor for gases containing reducing substances, said heatable gas sensor having a gas-sensitive porous metal oxide and electrical elements which are spaced a distance apart from one another and heat the metal oxide and measure a conductivity of the metal oxide, at least two electrical elements are each embedded in the sintered metal oxide and at least one of the electrical elements is designed for heating the metal oxide as well as for measuring the conductivity in cooperation with another electrical element, at least two electrical elements are arranged at a distance from one another by using supporting means and are embedded in gas-sensitive porous metal oxide, and the metal oxide is sintered.

7. The method according to claim 6, characterized in that the supporting means comprise a comb structure or wax or the like.

8. The method according to claim 6, characterized in that the supporting means (19) are removed before or after embedding in metal oxide.

9. The method according to claim 6, characterized in that the electrical elements are embedded in metal oxide powder.

10. The method according to claim 6, characterized in that the metal oxide powder is sintered with the embedded electrical elements.

11. The method according to claim 6, characterized in that first a layer of metal oxide powder is introduced into a mold, then the elements are placed a distance apart from one another on the layer of metal oxide powder, the elements are then covered with another layer of metal oxide powder, a pressure is applied and finally sintering is performed.

12. The method according to claim 6, characterized in that metal oxide powder is first introduced into a mold, an electrical element is applied to the metal oxide powder, the element is covered with a layer of metal oxide powder in the desired thickness, another element is applied, the additional element (18) is covered with metal oxide powder, a pressure is applied and then sintering is performed.

* * * * *